United States Patent
Hähnlein et al.

(10) Patent No.: US 6,264,986 B1
(45) Date of Patent: Jul. 24, 2001

(54) STABLE EMULSIONS AND DRY POWDERS OF MIXTURES OF FAT-SOLUBLE VITAMINS, THEIR PREPARATION AND USE

(75) Inventors: Wolfgang Hähnlein, Freinsheim (DE); Morten Mohr Hansen; Jes Elenius Olesen, both of Kopenhagen (DK); Anne Grethe Tobiasen, Snekkersten (DK)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 08/948,061

(22) Filed: Oct. 9, 1997

(30) Foreign Application Priority Data

Oct. 14, 1996 (DE) .............................. 196 42 359

(51) Int. Cl.⁷ ..................................... A61K 9/14
(52) U.S. Cl. ........................... 424/489; 426/73; 426/311; 514/167; 514/725; 560/260; 560/378
(58) Field of Search ..................... 424/484, 420, 424/489; 514/681, 167, 725; 426/73, 311; 560/260, 378

(56) References Cited

U.S. PATENT DOCUMENTS

| 2,756,177 | 7/1956 | Cannalonga et al. ................ 167/81 |
| 2,897,119 | 7/1959 | Dunn ...................................... 167/81 |
| 4,486,435 | * 12/1984 | Schmidt ............................... 424/252 |
| 4,670,247 | 6/1987 | Scialpi ................................. 424/484 |
| 4,966,779 | 10/1990 | Kirk ....................................... 426/72 |
| 5,350,773 | * 9/1994 | Schweikert ........................... 514/763 |
| 5,356,636 | * 10/1994 | Schneider ............................. 424/489 |
| 5,500,415 | * 3/1996 | Dollat .................................... 514/21 |
| 5,668,183 | 9/1997 | Leuenberger ......................... 514/725 |

FOREIGN PATENT DOCUMENTS

| 2194796 | 7/1995 | (CA) . |
| 285 682 | 10/1988 | (EP) . |
| 1576528 | 10/1980 | (GB) . |

OTHER PUBLICATIONS

Derwent Abstract of JP 58162517, Sep. 27, 1983.*

Derwent Abstract of CN–1116925, Feb. 21, 1996.*

Morton, "Fat Soluble Vitamins", *Intern. Encyc. of Food and Nutrition*, vol. 9, 1970, pp. 134–139 and 130–131.

* cited by examiner

Primary Examiner—Christopher S. F. Low
Assistant Examiner—David Lukton
(74) Attorney, Agent, or Firm—Keil & Weinkauf

(57) ABSTRACT

The present invention relates to stable emulsions and dry powders of mixtures of fat-soluble vitamins, and to processes for their preparation and to their use.

6 Claims, No Drawings

STABLE EMULSIONS AND DRY POWDERS OF MIXTURES OF FAT-SOLUBLE VITAMINS, THEIR PREPARATION AND USE

The present invention relates to novel stable emulsions and dry powders of mixtures of fat-soluble vitamins, and to a process for their preparation and to their use.

Fat-soluble vitamins play an important part in human and animal nutrition. It is common to these fat-soluble agents that, in their pure form, they can be handled only with difficulty or not at all because they are oxidation-sensitive substances. Furthermore, a fine dispersion of the agent is advantageous for optimal absorbability and thus bioavailability. These substances are therefore often supplied in the form of emulsions or preferably, in the form of dry powders, where the agents, either in pure form or as solution in a physiologically tolerated oil, are embedded in a fine dispersion in a protective colloid.

Dry powders of fat-soluble vitamins can be prepared on the basis of formulation processes disclosed in the literature, described comprehensively inter alia in R. A. Morton, Fat Soluble Vitamins, Intern. Encyclopedia of Food and Nutrition, Volume 9, Pergamon Press 1970, pages 134–139. These entail the fat-soluble vitamin being emulsified into an aqueous protective colloid solution, homogenized and subsequently dried, where appropriate in the presence of a coating material.

The protective colloids frequently used are the biopolymers described in the patents DE-A-1 123 084, U.S. Pat. Nos. 2,756,177, 4,670,247 and in EP-A-0 285 682, EP-A-0 565 989 and DE-A-44 24 085, such as gelatin, gum arabic, starch, lignin or else partially hydrolyzed soya protein, and other substances obtained from natural sources. A compilation of commercial protective colloids is likewise to be found in R. A. Morton, Fat Soluble Vitamins, Intern. Encyclopedia of Food and Nutrition, Volume 9, Pergamon Press 1970, pages 130/131.

When dry powders which comprise mixtures of fat-soluble vitamins whose composition is adapted to physiological requirements and in which the individual components are in some cases present in extremely large or small amounts relatively are used, the requirements to be met by the formulating are particularly stringent. In this case, it is particularly important for the user that, besides the required stability, a homogeneous equal dispersion of the agents in all the particles is ensured.

It is an object of the present invention to propose a process for preparing stable mixtures of fat-soluble vitamins in finely dispersed form. It was furthermore the intention to provide dry powders of fat-soluble vitamins in which, besides the required stability, a homogeneous equal dispersion of the agents in all the particles is ensured.

The term "fat-soluble vitamins" comprises for the purposes of the present invention in particular vitamins A, D, E and/or K, the corresponding provitamins and vitamin derivatives such as esters with an action resembling that of vitamin A, D, E or K, and the term "vitamin (A,D,E,K)" formulated in the claims likewise comprises their derivatives and a mixture thereof.

We have found that this object is achieved by a process for preparing a stable emulsion or a stable dry powder of fat-soluble vitamins which comprises emulsifying in each case separately in water:
a) vitamin K and
b) a mixture of vitamin D, vitamin E and vitamin A or an inert oil or a mixture of vitamin A and an inert oil, obtainable by
   $b_1$) dissolving vitamin D in an inert oil and/or vitamin A, and mixing with vitamin E, or
   $b_2$) adding vitamin D to a mixture of vitamin E and vitamin A and/or an inert oil,
carrying out the emulsification of components a) and b) in each case in the presence
c) of one or more protective colloids,
d) where appropriate of one or more sugars and/or sugar alcohols and
e) where appropriate other additives,
subsequently mixing the emulsions and drying the mixture to prepare a stable vitamin dry powder, where appropriate in the presence of a coating material.

If the vitamin mixture is formulated by the processes disclosed in the literature, in which first the fat-soluble vitamins are mixed and then emulsified into an aqueous protective colloid solution, homogenized and finally dried, the following phenomena are to be observed:

An oily mixture, prepared before the emulsification step, of vitamin K with vitamin A and/or vitamin E spontaneously becomes deep red. This red coloration is usually unwanted from the viewpoint of use.

It is furthermore found that a mixture of vitamin E and vitamin D in which vitamin E comprises more than 70% by weight results in extensive breakdown of vitamin D. Thus, for example, the loss of vitamin D activity measured in a mixture of 99.6 parts by weight of vitamin E and 0.4 part by weight of vitamin D is about 50%.

It is now possible with the aid of the process according to the invention to eliminate the stability problems and control the color of the dry powder as required. Thus, the intrinsic color of the vitamins is retained on separate emulsification of vitamin K on the one hand and the mixture of vitamin A, D and/or E on the other hand. Even on subsequent mixing of the two prepared emulsions there is retention of their pale yellow coloration.

It has been possible according to the invention to prevent the surprising losses of vitamin D activity in the presence of large amounts of vitamin E by first dissolving vitamin D in vitamin A and/or an inert oil, subsequently adding vitamin E to the resulting solution with the parts by weight of vitamin A and/or the inert oil being at least 25%, preferably greater than 50%, especially more than 100%, of the parts by weight of vitamin E. In another variant of the process for stabilizing vitamin D, the concentration of vitamin E is first reduced by "dilution" with at least 25% by weight, preferably more than 50% by weight, of vitamin A and/or an inert oil, and subsequently vitamin D is added to this mixture.

For certain applications, eg. for coloring human foods or drugs, a stable formulation of the abovementioned red vitamin mixture is advantageous. A product of this type is obtained by a process according to the invention which comprises emulsifying a mixture of
a) vitamin D, vitamin E and vitamin K, and vitamin A or an inert oil or a mixture of vitamin A and an inert oil, obtainable by
   $a_1$) dissolving vitamin D in an inert oil and/or vitamin A, and mixing with vitamin E and vitamin K, or
   $a_2$) adding vitamin D to a mixture of vitamin E and vitamin K, and vitamin A and/or an inert oil, in the presence
c) of one or more protective colloids.
d) where appropriate of one or more sugars and/or sugar alcohols and
e) where appropriate of other additives,
in water and drying the emulsion to prepare a stable vitamin dry powder, where appropriate in the presence of a coating material.

Whereas this variant of the preparation also ensures, by process step $a_1$) or $a_2$), the stability of vitamin D, the mixing of vitamin E with vitamin K before the emulsification produces a dark red oil whose color characterizes the later emulsion and the dry powder obtained after drying.

The mixture of fat-soluble vitamins employed in both variants of the process according to the invention is composed of 5–90% by weight of vitamin A and/or an inert oil, 5–90% by weight of vitamin E, 0.01–1% by weight of vitamin D and 0.1–10% by weight of vitamin K, where the % by weight data for the individual components add up to 100%.

A particular embodiment of the abovementioned process is one when the vitamin mixture contains 25–70% by weight of vitamin A and/or an inert oil, 30–70% by weight of vitamin E, 0.05–0.4% by weight of vitamin D and 2–8% by weight of vitamin K, where the % by weight data for the individual components add up to 100%.

Since the two abovementioned processes according to the invention result in stable emulsions and dry powders of mixtures of the fat-soluble vitamins A, D, E and K and of vitamins D, E and K, the aim was also to find solutions for the stability problems with the following ternary combinations, namely of vitamins A, D, K; of vitamins A, E, K and of vitamins A, D, E.

This object has been achieved by the following processes for preparing stable vitamin emulsions and dry powders, which comprise 1) for the vitamin A, D and K ternary combination emulsifying in each case separately in water:
   a) vitamin K and
   b) a mixture of vitamin D and vitamin A,
      carrying ot the emulsification of components a) and b) in each case in the presence
   c) of one or more protective colloids,
   d) where appropriate of one or more sugars and/or sugar alcohols and
   e) where appropriate of other additives,
subsequently mixing the emulsions and drying the mixture to prepare a stable vitamin dry powder, where appropriate in the presence of a coating material.

2) for the vitamin A, D and K ternary combination emulsifying:
   a) a mixture of vitamin A, vitamin K and vitamin D in the presence
   c) of one or more protective colloids,
   d) where appropriate of one or more sugars and/or sugar alcohols and
   e) where appropriate of other additives in water,
and drying the emulsion to prepare a stable vitamin dry powder, where appropriate in the presence of a coating material.

3) for the vitamin A, E and K ternary combination emulsifying in each case separately in water:
   a) vitamin K and
   b) a mixture of vitamin A and vitamin E,
      carrying out the emulsification of components a) and b) in each case in the presence
   c) of one or more protective colloids,
   d) where appropriate of one or more sugars and/or sugar alcohols and
   e) where appropriate of other additives,
subsequently mixing the emulsions, and drying the mixture to prepare a stable vitamin dry powder, where appropriate in the presence of a coating material.

4) for the vitamin A, E and K ternary combination emulsifying:
   a) a mixture of vitamin A, vitamin E and vitamin K in the presence
   c) of one or more protective colloids,
   d) where appropriate of one or more sugars and/or sugar alcohols and
   e) where appropriate of other additives,
in water and drying the emulsion to prepare a stable vitamin dry powder, where appropriate in the presence of a coating material.

5) for the vitamin A, D and E ternary combination emulsifying a mixture of
   a) vitamin D, vitamin E and vitamin A or an inert oil or a mixture of vitamin A and an inert oil, obtainable by
      $a_1$) dissolving vitamin D in an inert oil and/or vitamin A, and mixing with vitamin E, or
      $a_2$) adding vitamin D to a mixture of vitamin E and vitamin A and/or an inert oil, in the presence
   c) of one or more protective colloids,
   d) where appropriate of one or more sugars and/or sugar alcohols and
   e) where appropriate other additives,
in water, and drying the emulsion to prepare a stable vitamin dry powder, where appropriate in the presence of a coating material.

The mixture of fat-soluble vitamins employed in processes 1) and 2) according to the invention is composed of 70–98% by weight of vitamin A, 0.01–1% by weight of vitamin D and 2–30% by weight of vitamin K.

The mixtures of fat-soluble vitamins employed in processes 3) and 4) have the following composition: 5–90% by weight of vitamin A, 5–90% by weight of vitamin E and 0.1–10% by weight of vitamin K.

The vitamin mixture employed in process 5) according to the invention is composed of 5–90% by weight of vitamin A and/or an inert oil, 5–90% by weight of vitamin E and 0.01–1% by weight of vitamin D, where the % by weight data for each of the abovementioned individual components add up to 100%.

All five of the variants of the process detailed above for preparing emulsions and dry powders of fat-soluble vitamins which, by definition, comprise a ternary combination from the group of vitamins A, D, E and K result in stable products whose color can be adjusted as required by the particular emulsification process according to the invention.

When carrying out the processes according to the invention, the fat-soluble vitamins are mixed in the first process step, with, in the case of the vitamin combinations A, D, E, K; D, E, K; A, D, E and D and E, first a solution of vitamin D in vitamin A and/or an inert oil being prepared at elevated temperature, eg. at from about 40° C. to 80° C., preferably 50° C. to 70° C. The remaining vitamins are then added to this solution, and it is emulsified into an aqueous protective colloid solution at 50° C. to 70° C.

However, it is also possible first to mix vitamin E with vitamin A, vitamin K and/or an inert oil at the abovementioned temperatures in order thus to reduce the concentration of vitamin E and only then to add vitamin D to this mixture and subsequently emulsify it into an aqueous protective colloid solution.

In the cases where a red coloration of the vitamin emulsion is unwanted when vitamin K is present, it is advantageous to emulsify both vitamin K and the mixture of vitamins A, E and/or D and, where appropriate, an inert oil in each case separately under the abovementioned conditions and subsequently to mix these emulsions.

After homogenization and adjustment of the viscosity of the emulsion(s) to 50 to 300 cP, preferably 70 to 150 cP, by appropriate dilution with water, the emulsion(s) can be converted into a powder product in a conventional way, eg. by spray drying or by spray cooling or by spraying the emulsion in a spray tower also using an inert coating material, collecting the coated particles and drying in a fluidized bed.

The stable vitamin dry powders prepared by the process according to the invention contain 3–40% by weight of a mixture of vitamin A, vitamin D, vitamin E and/or vitamin K and/or an inert oil, 5–40% by weight of a protective colloid, 0–30% by weight of a sugar and/or sugar alcohol, 0–70% by weight of a coating material and, where appropriate, 0–25% by weight of other additives, where the % by weight data for the individual components add up to 100%.

The term "inert oil" means physiologically acceptable oils such as sesame oil, corn oil, cottonseed oil, coconut oil, soybean oil or peanut oil, and esters of medium chain-length vegetable fatty acids.

Examples of protective colloids which are used are gelatin, fish gelatin, starch, dextrin, vegetable proteins, pectin, gum arabic, casein, caseinate or mixtures thereof, preferably employing gelatin, gum arabic, vegetable proteins and/or modified starch. However, polyvinyl alcohol, polyvinylpyrrolidone, methylcellulose, carboxymethylcellulose, hydroxypropylcellulose and alginates are also conceivable as preferable protective colloids. For further details, reference is made to R. A. Morton, Fat Soluble Vitamins, Intern. Encyclopedia of Food and Nutrition, Volume 9, Pergamon Press 1970, pages 128–131. To increase the mechanical stability of the final product, it is expedient to add a plasticizer to a colloid, such as sugars or sugar alcohols, eg. sucrose, glucose, fructose, lactose, invert sugar, sorbitol, mannitol, maltodextrin or glycerol. In preferred embodiments of the process according to the invention, sucrose, lactose and/or maltodextrin are employed.

Other additives which can be added to increase the stability of the agents to oxidative degradation are stabilisers such as t-butylhydroxytoluene, t-butylhydroxyanisole, ascorbic acid or ethoxyquin. They are preferably emulsified together with the vitamins and, where appropriate, additional emulsifiers into the aqueous protective colloid solution. Examples of emulsifiers which can be used are ascorbyl palmitate, polyglycerol fatty acid esters, sorbitan fatty acid esters, propylene glycol fatty acid esters or lecithin.

The term coating material means compounds such as starch and/or starch derivatives, and silica and/or silica derivatives, with whose aid the vitamin dry powders are physically stabilized. Preferred coating materials in the human food sector are starch or starch derivatives, especially corn or rice starch.

The products according to the invention can be used both as additives to human foods and drugs and for livestock nutrition. In certain cases, it may also be expedient to use the prepared emulsions directly as such, without converting them into dry powders.

The following examples explain the processes according to the invention in detail.

EXAMPLE 1 a) Preparation of the vitamin mixture:

1.7 g (40 million IU/g) of vitamin $D_3$ were dissolved by stirring at 65° C. in 500 g (1.7 million IU/g) of preheated vitamin A palmitate, and subsequently 500 g (1,100 IU/g) of d,l-α-tocopherol and 45 g of vitamin $K_1$ were added at 65° C.

b) Preparation of the emulsion:

2 kg of gum arabic and 2 kg of sucrose were dissolved in 9 kg of distilled water at 65° C. in an emulsifying container. After stirring for 30 minutes, the vitamin mixture was added and the mixture was homogenized for a further 2 h. Subsequently, the emulsion was diluted with water until the viscosity was about 100 cP, and was enveloped in starch and dried in a spray tower.

A yellowish brown vitamin dry powder with the following vitamin content was obtained:

Vitamin A palmitate: 91,000 IU/g
Vitamin $D_3$: 7090 IU/g
Vitamin $K_1$: 0.41%
d,l-α-tocopherol: 4.88%

EXAMPLE 2 a) Preparation of the vitamin mixture:

1.7 g (40 million IU/g) of vitamin $D_3$ were dissolved at 65° C. by stirring in 50 g (1,100 IU/g) d,l-α-tocopherol, and subsequently 500 g (1.7 million IU/g) of vitamin A palmitate were added at 65° C.

b) Preparation of the emulsion:

2 kg of gum arabic and 2 kg of sucrose were dissolved in 9 kg of distilled water at 65° C. in an emulsifying container. After stirring for 30 minutes, 500 g of the solution were transferred into a 1 l reactor and homogenized with 45 g of vitamin $K_1$. The remaining protective colloid solution was mixed with the vitamin mixture from a) and homogenized for about 2 h. The two emulsions were slowly mixed in a separate emulsifying container, diluted with water to a viscosity of about 100 cP, and enveloped in starch and dried in a spray tower.

A pale yellow vitamin dry powder with the following vitamin content was obtained:

Vitamin A palmitate: 72,000 IU/g
Vitamin $D_3$: 3340 IU/g
Vitamin $K_1$: 0.44%
d,l-α-tocopherol: 4.17%

The content of vitamin $D_3$ fell to about 50% of the amount originally employed.

EXAMPLE 3 a) Preparation of the vitamin mixture:

1.7 g (40 million IU/g) of vitamin $D_3$ were dissolved by stirring in 500 g (1.7 million IU/g) of vitamin A palmitate at 65° C. and subsequently 500 g (1,100 IU/g) of d,l-α-tocopherol were added.

b) Preparation of the emulsion:

2 kg of gum arabic and 2 kg of succrose were dissolved in 9 kg of distilled water at 65° C. in an emulsifying container. After stirring for 30 minutes, 500 g of the solution were transferred into a 1 l reactor and homogenized with 45 g of vitamin $K_1$. The remaining protective colloid solution was mixed with the vitamin mixture from a) and homogenized for about 2 h. The two emulsions were slowly mixed in a separate emulsifying container, diluted with water to a viscosity of about 100 cP, and enveloped in starch and dried in a spray tower.

The pale yellow vitamin dry powder had the following vitamin content:

Vitamin A palmitate: 103,000 IU/g
Vitamin $D_3$: 7540 IU/g
Vitamin $K_1$: 0.49%
d,l-α-tocopherol: 4.68%

EXAMPLE 4 a) Preparation of the vitamin mixture:

1.7 g (40 million IU/g) of vitamin $D_3$ were dissolved by stirring in 65 g of fractionated coconut oil, and subsequently a mixture, at 65° C., of 500 g (1.7 million IU/g) of vitamin A palmitate and 500 g (1,100 IU/g) of d,l-α-tocopherol was added.

b) Preparation of the emulsion:

2 kg of gum arabic and 2 kg of sucrose were dissolved in 9 kg of distilled water at 65° C. in an emulsifying container. After stirring for 30 minutes, 500 g of the solution were transferred into a 1 l reactor and homogenized with 45 g of vitamin $K_1$. The remaining protective colloid solution was mixed with the vitamin mixture from a) and homogenized for about 2 h. The two emulsions were slowly mixed in a separate emulsifying container, diluted with water to a viscosity of about 100 cP, and enveloped in starch and dried in a spray tower.

The pale yellow vitamin dry powder had the following vitamin content:
Vitamin A palmitate: 71,600 IU/g
Vitamin $D_3$: 5850 IU/g
Vitamin $K_1$: 0.36%
d,l-α-tocopherol: 3.96%

EXAMPLE 5 a) Preparation of the vitamin mixture:

1.2 g (40 million IU/g) of vitamin $D_3$ were dissolved by stirring in 350 g (1.7 million IU/g) of vitamin A palmitate at 65° C., subsequently 350 g (1,100 IU/g) of d,l-α-tocopherol were added.

b) Preparation of the emulsion:

1.4 kg of starch modified with sodium octenyl succinate and 1.4 kg of sucrose were dissolved in 6.3 kg of distilled water at 65° C. in an emulsifying container. After stirring for 30 minutes, 500 g of the solution were transferred into a 1 l reactor and homogenized with 33 g of vitamin $K_1$. The remaining protective colloid solution was mixed with the vitamin mixture from a) and homogenized for about 2 h. The two emulsions were slowly mixed in a separate emulsifying container, diluted with water to a viscosity of about 100 cP and then enveloped in starch and dried in a spray tower.

The pale yellow vitamin dry powder had the following vitamin content:
Vitamin A palmitate: 85,300 IU/g
Vitamin $D_3$: 7080 IU/g
Vitamin $K_1$: 0.44%
d,l-α-tocopherol: 4.78%

EXAMPLE 6 a) Preparation of the vitamin mixture:

2.6 g (40 million IU/g) of Vitamin $D_3$ were dissolved by stirring at 65° C. in 750 g (1.7 million IU/g) of preheated vitamin A palmitate, and then 750 g (1,100 IU/g) of d,l-α-tocopherol were added at 65° C.

b) Preparation of the emulsion:

2 kg of sodium caseinate and 4 kg of sucrose were dissolved in 7 kg of distilled water at 65° C. in an emulsifying container. After stirring for 30 minutes, 500 g of the solution were transferred into a 1 l reactor and homogenized with 68 g of vitamin $K_1$. The remaining protective colloid solution was mixed with the vitamin mixture from a) and homogenized for about 2 h. The two emulsions were slowly mixed in a separate emulsifying container, diluted with water to a viscosity of about 100 cP, and enveloped in starch and dried in a spray tower.

The pale yellow vitamin dry powder had the following vitamin content:
Vitamin A palmitate: 86,500 IU/g
Vitamin $D_3$: 6950 IU/g
Vitamin $K_1$: 0.47%
d,l-α-tocopherol: 4.8%

EXAMPLE 7

Preparation of the vitamin mixture:

1.,7 g (40 million IU/g) of vitamin $D_3$ were dissolved by stirring at 65° C. in 500 g (1,100 IU/g) of d,l-α-tocopherol, and then 500 g (1.7 million IU/g) of vitamin A palmitate at 65° C. were added. The mixture was subsequently cooled to 4° C. and stored at this temperature for 2 weeks. After 4 and 10 days, the contents of vitamins in the mixture were determined.

|  | calculated | measured |
| --- | --- | --- |
| 4 days |  |  |
| Vitamin A palmitate | 850,000 IU/g | 848,000 IU/g |
| Vitamin $D_3$ | 66,000 IU/g | 33,500 IU/g |
| d,l-α-tocopherol | 49.9% | 50.0% |
| 10 days |  |  |
| Vitamin $D_3$ | 66,000 IU/g | 33,500 IU/g |

EXAMPLE 8

The amounts of vitamin $D_3$ (40 million IU/g) listed in Table 1 or a solution of vitamin $D_3$ in fractionated coconut oil were mixed with various amounts of d,l-α-tocopherol (1,100 IU/g) by stirring at 65° C. A sample of the mixture was analyzed for its vitamin D content immediately after preparation. One half of the remaining vitamin mixture was in each case stored at 65° C. for 24 hours and the second half was stored at 5° C. for 24 hours. The two halves were subsequently investigated for their vitamin $D_3$ content.

TABLE 1

| Experiment | Vitamin D [mg] | Coconut oil [g] | Vitamin E [g] | Vit. D content (5 min, 65° C.) [% of th.] | Vit. D content (24 h, 65° C.) [% of th.] | Vit. D content (24 h, 5° C.) [% of th.] |
| --- | --- | --- | --- | --- | --- | --- |
| 1 | 52.9 |  | 14.90 | 69 | 2 | 61 |
| 2 | 52.3 | 3.68 | 10.90 | 89 | 50 | 90 |
| 3 | 51.1 | 7.28 | 7.30 | 93 | 87 | 93 |
| 4 | 54.9 | 10.99 | 3.68 | 94 | 86 | 90 |

We claim:

1. A process for preparing a stable dry powder containing vitamins A, D and K, wherein said process comprises:
   a) emulsifying vitamin K in an aqueous solution containing one or more protective colloids;
   b) emulsifying a mixture of vitamins A and D in an aqueous solution containing one or more protective colloids;
   c) combining the emulsions from steps a) and b);
   d) drying the mixture of step c) to yield a dry powder, optionally in the presence of a coating material;
   with the proviso that in step a) the aqueous solution does not contain vitamin A.

2. The process of claim 1, wherein the aqueous solution of step a) or b) further comprises one or more sugars and optionally one or more other additives.

3. The process of claim 1, wherein the dry powder of step d) contains from 70–98% by weight of vitamin A, from 0.01–1% by weight of vitamin D and from 2—30% by weight of vitamin K, wherein the weight % of said vitamins totals 100%.

4. A process for preparing a stable emulsion containing vitamins A, D and K, wherein said process comprises:

a) emulsifying vitamin K in an aqueous solution containing one or more protective colloids;
b) emulsifying a mixture of vitamins A and D in an aqueous solution containing one or more protective colloids; and
c) combining the emulsions from steps a) and b);

with the proviso that in step a) the aqueous solution does not contain vitamin A.

5. The process of claim 4, wherein the aqueous solution of step a) or b) further comprises one or more sugars and optionally one or more other additives.

6. The process of claim 5, wherein the combined emulsion resulting from step c) contains from 70–98% by weight of vitamin A, from 0.01–1% by weight of vitamin D and from 2–30% by weight of vitamin K, wherein the weight % of said vitamins totals 100%.

* * * * *